United States Patent
Lensing et al.

(10) Patent No.: US 6,766,215 B1
(45) Date of Patent: Jul. 20, 2004

(54) METHOD AND APPARATUS FOR DETECTING NECKING OVER FIELD/ACTIVE TRANSITIONS

(75) Inventors: Kevin R. Lensing, Austin, TX (US); Marilyn I. Wright, Austin, TX (US)

(73) Assignee: Advanced Micro Devices, Inc., Austin, TX (US)

( * ) Notice: Subject to any disclaimer, the term of this patent is extended or adjusted under 35 U.S.C. 154(b) by 15 days.

(21) Appl. No.: 10/610,942

(22) Filed: Jul. 1, 2003

Related U.S. Application Data

(62) Division of application No. 09/863,598, filed on May 23, 2001, now Pat. No. 6,657,716.

(51) Int. Cl.[7] .................................. G06F 19/00
(52) U.S. Cl. ........................................ 700/121
(58) Field of Search .................... 438/14, 76; 700/121; 356/237.5; 430/30

(56) References Cited

U.S. PATENT DOCUMENTS

| | | | |
|---|---|---|---|
| 6,245,584 B1 * | 6/2001 | Marinaro et al. | 438/14 |
| 6,303,395 B1 * | 10/2001 | Nulman | 438/14 |
| 6,424,880 B1 * | 7/2002 | Goder et al. | 700/121 |
| 6,684,122 B1 * | 1/2004 | Christian et al. | 700/121 |

* cited by examiner

Primary Examiner—John F. Niebling
Assistant Examiner—Andre' Stevenson
(74) Attorney, Agent, or Firm—Williams, Morgan & Amerson, P.C.

(57) ABSTRACT

A method and an apparatus for detecting a necking error during semiconductor manufacturing. At least one semiconductor wafer is processed. Metrology data from the processed semiconductor wafer is acquired. Data from a reference library comprising optical data relating to a poly-silicon formation on a semiconductor wafer is accessed. The metrology data is compared to data from the reference library. A fault-detection analysis is performed in response to the comparison of the metrology data and the reference library data.

9 Claims, 11 Drawing Sheets

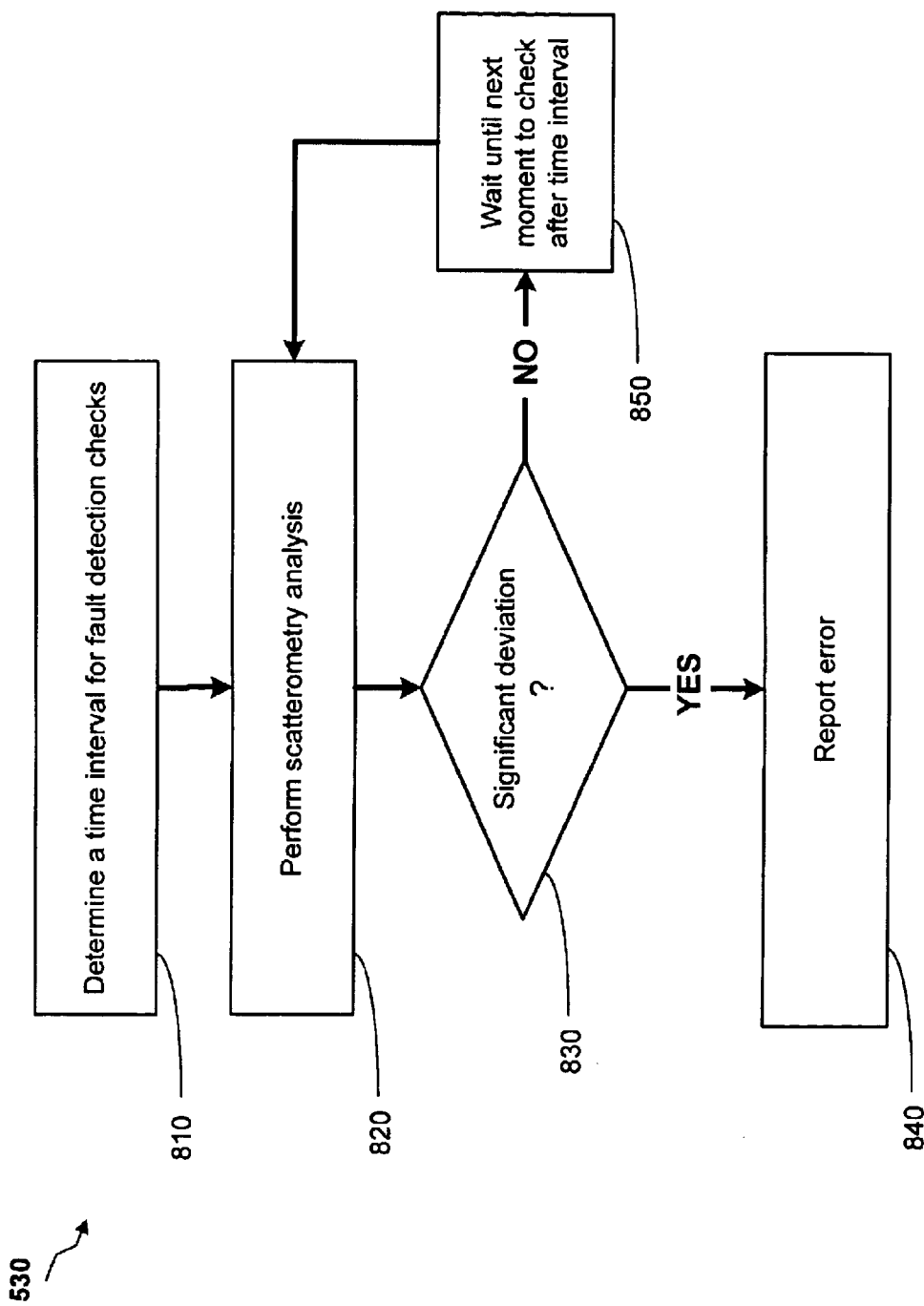

METHOD AND APPARATUS FOR DETECTING NECKING OVER FIELD/ACTIVE TRANSITIONS

This is a divisional of Application Ser. No. 09/863,598 filed May 23, 2001, now U.S. Pat. No. 6,657,716.

BACKGROUND OF THE INVENTION

1. Field of the Invention

This invention relates generally to semiconductor manufacturing, and, more particularly, to a method and apparatus for detecting necking effects over a field/active transition region. 2. Description of the Related Art The technology explosion in the manufacturing industry has resulted in many new and innovative manufacturing processes. Today's manufacturing processes, particularly semiconductor manufacturing processes, call for a large number of important steps. These process steps are usually vital, and therefore, require a number of inputs that are generally fine-tuned to maintain proper manufacturing control.

The manufacture of semiconductor devices requires a number of discrete process steps to create a packaged semiconductor device from raw semiconductor material. The various processes, from the initial growth of the semiconductor material, the slicing of the semiconductor crystal into individual wafers, the fabrication stages (etching, doping, ion implanting, or the like), to the packaging and final testing of the completed device, are so different from one another and specialized that the processes may be performed in different manufacturing locations that contain different control schemes.

Generally, a set of processing steps is performed on a group of semiconductor wafers, sometimes referred to as a lot, using a semiconductor manufacturing tool called an exposure tool or a stepper. Typically, an etch process is then performed on the semiconductor wafers to shape objects on the semiconductor wafer, such as polysilicon lines, each of which may function as a gate electrode for a transistor. As another example, a plurality of metal lines, e.g., aluminum, may be formed that serve as conductive lines that connect one conductive region on the semiconductor wafer to another. The manufacturing tools communicate with a manufacturing framework or a network of processing modules. Each manufacturing tool is generally connected to an equipment interface. The equipment interface is connected to a machine interface to which a manufacturing network is connected, thereby facilitating communications between the manufacturing tool and the manufacturing framework. The machine interface can generally be part of an advanced process control (APC) system. The APC system initiates a control script, which can be a software program that automatically retrieves the data needed to execute a manufacturing process.

FIG. 1 illustrates a typical semiconductor wafer 105. The wafer 105 typically includes a plurality of individual semiconductor die arranged in a grid 150. Photolithography steps are typically performed by a stepper on approximately one to four die locations at a time, depending on the specific photomask employed. Photolithography steps are generally performed to form patterned layers of photoresist above one or more process layers that are to be patterned. The patterned photoresist layer can be used as a mask during etching processes, wet or dry, performed on the underlying layer or layers of material, e.g., a layer of polysilicon, metal or insulating material, to transfer the desired pattern to the underlying layer. The patterned layer of photoresist is comprised of a plurality of features, e.g., line-type features, such as a polysilicon line, or opening-type features, that are to be replicated in an underlying process layer.

Turning now to FIG. 2 a silicon substrate 210 that contains a plurality of layers 220, 230, is shown. In one embodiment, a layer of silicon dioxide or silicon nitride is added on the surface 215 of the silicon substrate 220. The formation shown in FIG. 2A contains two layers 220, 230 that intersect at different heights, causing a step down from layer 220 to layer 230. A poly-silicon line formation 240 is formed above the layers 220, 230. In one embodiment, the poly-silicon line 240 is formed using an etch process. When an etch process is used to form the poly-silicon line 240, the step down from layer 220 to layer 230, can cause a necking effect on the poly-silicon line 240. That is, the step down from layer 220 to layer 230 may tend to cause a reduction in the width of the polysilicon line 240. The reduction in the polysilicon line 240 may occur in the direction indicated by the arrows 242, or may occur in the manner illustrated in FIG. 2B An illustration of a necking effect on the poly-silicon line 240 is shown in FIG. 2B, whereby the poly-silicon line 240 is thinner at the intersection 260 of layer 220 and layer 230. Many times, the necking effect on the poly-silicon line 240, can cause the poly-silicon line 240 to become too thin at the step down intersection 260 of layers 220 and 230. Furthermore, the necking effect shown in FIG. 2B can cause the poly-silicon line 240 to break, which can destroy electrical connections facilitated by the poly-silicon line 240. This effect can cause significant yield problems in the manufacturing of semiconductor devices.

Tests that are used for detecting poly-silicon line 240 breaking and necking effects are destructive in nature and can be very time consuming. Often, the tests that are used to detect necking and poly-silicon line 240 breakage problems can cause interruptions in the production line during semiconductor manufacturing processes.

The necking effect experienced by the poly-silicon line 240 can cause quality degradation of the wafer 105 being processed. For example, the poly-silicon line 240 experiencing the necking effect can become unreliable. Many times, the poly-silicon line 240 breaks at the transition region 260 due to the necking effect experienced by the poly-silicon line. Conventional methods to examine the necking effect experienced by the poly-silicon line 240 can be inefficient or destructive.

The present invention is directed to overcoming, or at least reducing the effects of, one or more of the problems set forth above.

SUMMARY OF THE INVENTION

In one aspect of the present invention, a method is provided for detecting a necking error during semiconductor manufacturing. At least one semiconductor wafer is processed. Metrology data from the processed semiconductor wafer is acquired. Data from a reference library comprising optical data relating to a poly-silicon formation on a semiconductor wafer is accessed. The metrology data is compared to data from the reference library. A fault-detection analysis is performed in response to the comparison of the metrology data and the reference library data.

In another aspect of the present invention, a system is provided for detecting a necking error during semiconductor manufacturing. The system of the present invention comprises: a computer system; a manufacturing model coupled with the computer system, the manufacturing model being capable of generating and modifying at least one control input parameter signal; a machine interface coupled with the manufacturing model, the machine interface being capable of receiving process recipes from the manufacturing model; a processing tool capable of processing semiconductor wafers and coupled with the machine interface, the first processing tool being capable of receiving at least one control input parameter signal from the machine interface; a metrology tool coupled with the first processing tool and the second processing tool, the metrology tool being capable of acquiring metrology data; a scatterometry reference library, the scatterometry reference library comprising optical data related to a plurality of poly-silicon structures; and a scatterometry data error analysis unit coupled to the metrology tool and the scatterometry reference library, the scatterometry data error analysis unit capable of comparing the metrology data to corresponding data in the scatterometry reference library and calculating at least one of a necking error and a poly-silicon structure break error in response to the comparison.

BRIEF DESCRIPTION OF THE DRAWINGS

The invention may be understood by reference to the following description taken in conjunction with the accompanying drawings, in which like reference numerals identify like elements, and in which:

FIG. 8 illustrates a flowchart depiction of a method of performing a fault detection analysis described in FIG. 5, in accordance with one embodiment of the present invention;

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

There are many discreet processes that are involved in semiconductor manufacturing. Many times, semiconductor devices are stepped through multiple manufacturing process tools. Errors that can occur during the formation of poly-silicon structures on semiconductor wafers being processed can cause significant degradation of the wafers being manufactured. Embodiments of the present invention utilize an optical data acquisition tool, such as a scatterometer, ellipsometer, and the like, to detect and/or to reduce necking effects of poly-silicon structures formed on semiconductor wafers. Embodiments of the present invention can also be used to reduce breaks in poly-silicon structures.

Figure 3:
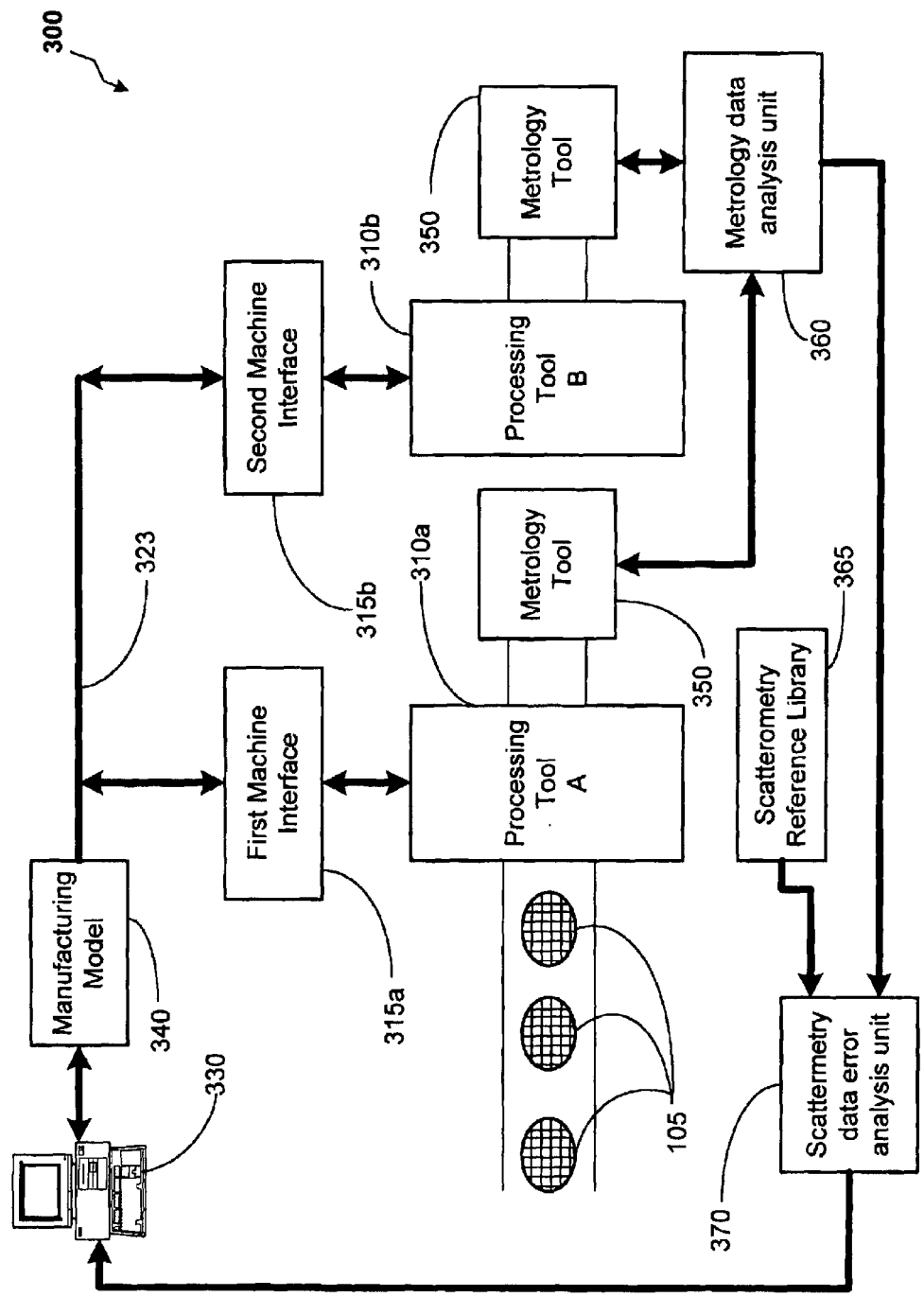
FIG. 3 is a block diagram representation of the system in accordance with one embodiment of the present invention.

Semiconductor devices are processed in a manufacturing environment using a number of input control parameters. Turning now to FIG. 3, a system 300 in accordance with one embodiment of the present invention is illustrated. In one embodiment, semiconductor wafers 105, are processed on processing tools 310a, 310b using a plurality of control input signals, or manufacturing parameters, on a line 323. In one embodiment, control input signals, or manufacturing parameters, on the line 323 are sent to the processing tools 310a, 310b from a computer system 330 via machine interfaces 315a, 315b. In one embodiment, the first and second machine interfaces 31a, 315b are located outside the processing tools 310a, 310b. In an alternative embodiment, the first and second machine interfaces 315a, 315b are located within the processing tools 310a, 310b.

In one embodiment, the computer system 330 sends control input signals, or manufacturing parameters, on the line 323 to the first and second machine interfaces 315a, 315b. The computer system 330 employs a manufacturing model 340 to generate the control input signals on the line 323. In one embodiment, the manufacturing model 340 contains a manufacturing recipe that determines a plurality of control input parameters that are sent on the line 323.

In one embodiment, the manufacturing model 340 defines a process script and input control that implement a particular manufacturing process. The control input signals on the line 323 that are intended for processing tool A 320a are received and processed by the first machine interface 315a. The control input signals on the line 323 that are intended for processing tool B 320b are received and processed by the second machine interface 315b. Examples of the processing tools 320a, 320b used in semiconductor manufacturing processes are steppers, step-and-scan tools, etch process tools, and the like.

One or more of the semiconductor wafers 105 that are processed by the processing tools 310a, 310b can also be sent to a metrology tool 350 for acquisition of metrology data. The metrology tool 350 can be a scatterometry data acquisition tool, an overlay-error measurement tool, a critical dimension measurement tool, and the like. In one embodiment, one or more processed semiconductor wafers 105 are examined by a metrology tool 350. Data from the metrology tool 350 is collected by a metrology data analyzer unit 360. The metrology data analyzer unit 360 organizes, analyses, and correlates scatterometry metrology data acquired by the metrology tool 350, to particular semiconductor wafers 105 that were examined. The metrology data analyzer unit 360 can be a software unit, a hardware unit, or a firmware unit. In one embodiment, the metrology data analyzer unit 360 is integrated into the computer system 330 or may be integrated into the metrology tool 350.

The system 300 comprises a scatterometry reference library 365. In one embodiment, the scatterometry reference library 365 comprises data relating to calculated optical data of a plurality of structures on a semiconductor wafer 105. In an alternative embodiment, the scatterometry reference library 365 comprises data relating to reflected optical data that occurs in response to optical stimuli engaged upon particular structures on a semiconductor wafer 105. A record that contains the response to optical stimuli performed on a plurality of structures, can be organized and stored in the scatterometry reference library 365, and used as reference for comparison of actual wafer data during manufacturing processes.

The particular reflection profile expected for any structure on a semiconductor wafer 105 depends on the specific geometry of the structure and the parameters of the measurement technique employed by the metrology tool 350, such as a scatterometry tool. The reflection profile for a particular structure includes the bandwidth of the reflected light, the angle of incidence, the intensity and phase of detected light, and the like. The profiles in the scatterometry reference library 365 are typically calculated theoretically by employing Maxwell's equations based on the characteristics of the structures on the semiconductor wafer 105. It is also contemplated that profiles in the scatterometry reference library 365 may be confirmed empirically by measuring reflection profiles of sample wafers and subsequent characterization of the measured wafers by destructive or non-destructive examination techniques.

A scatterometry error analysis unit 370 is capable of comparing the metrology data from the metrology data acquisition unit 360 to corresponding data from the scatterometry reference library 365 and determining if a significant error exists on the structure being analyzed. In one embodiment, the scatterometry error analysis unit 370 is a software unit that resides within the computer system 330. In an alternative embodiment, the scatterometry error analysis unit 370 is a hardware unit that is integrated into the system 300. In yet another embodiment, the scatterometry error analysis unit 370 is a firmware unit integrated within the system 300. The scatterometry error analysis unit 370 can be used by the system 300 to perform fault analysis of the semiconductor wafers 105 being manufactured, which is described in greater detail below. The scatterometry error analysis unit 370 can also be used by the system 300 feedback process control, which is described in greater detail below.

Figure 4A:
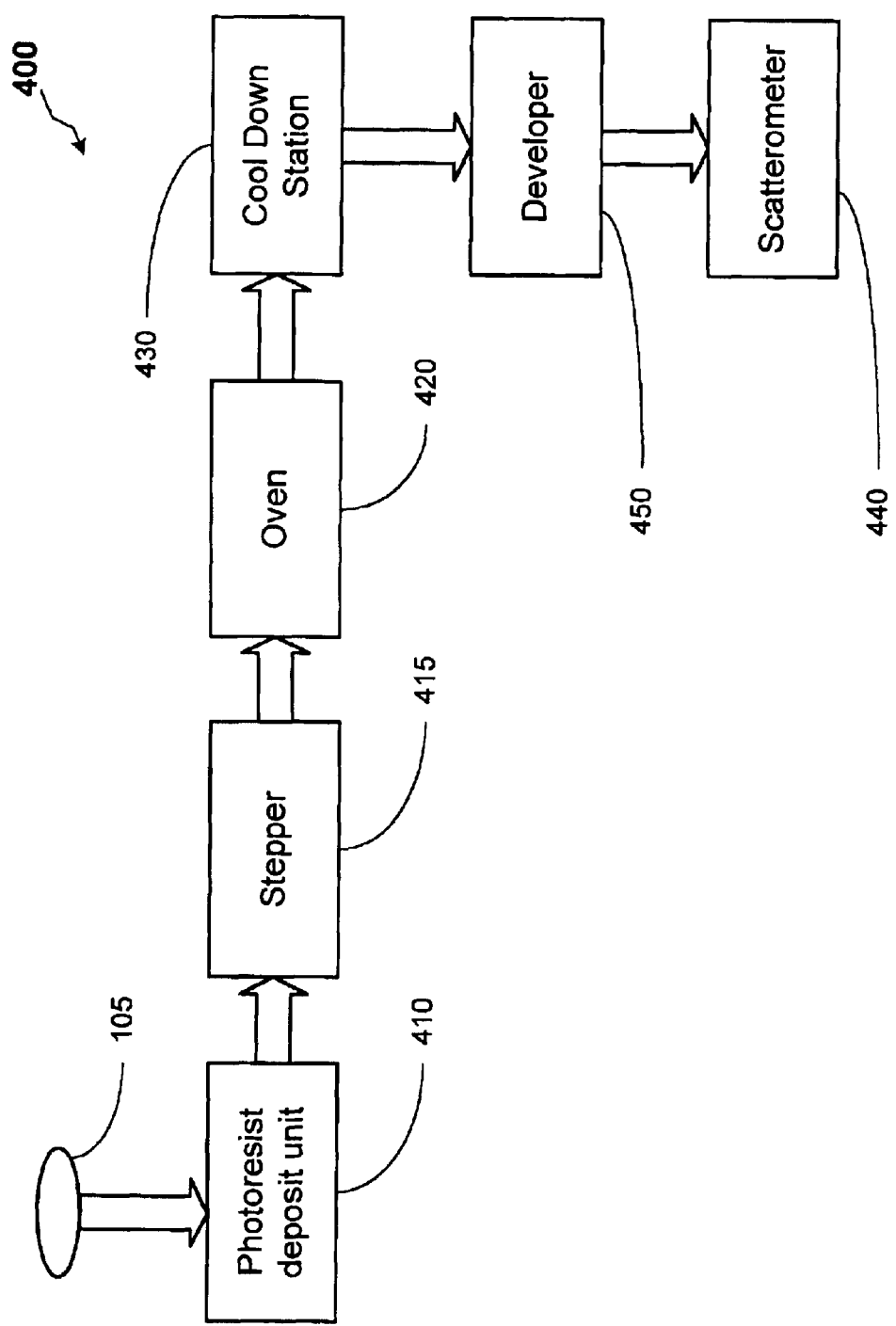
FIG. 4A illustrates one embodiment of a process flow in accordance with one embodiment of the present invention.

One embodiment of an implementation of a scatterometry metrology sequence in the context of semiconductor wafer manufacturing, is shown in FIG. 4A, wherein an illustrative processing line 400 for performing photolithography patterning is depicted. The processing line 400 includes a photoresist deposition unit 410, a stepper 415, an oven 420, a cool down station 430, a developer 450, and a scatterometer 440. The photoresist deposition unit 410 receives a semiconductor wafer 105, and forms a layer of photoresist of a predetermined thickness of above a process layer formed above the surface of the wafer 105. The stepper 415 then receives the wafer 105 and exposes the photoresist to a light source using a reticle to pattern the layer of photoresist. The wafer 105 is transferred to the oven 420, where a post exposure bake process is conducted. Following the post exposure bake, the wafer 105 is transferred to the cool down station 430, and then to the developer station 450 after the wafer 105 has sufficiently cooled. The soluble photoresist material is removed from the wafer 105 in the developer station 450, thereby resulting in a patterned layer of photoresist.

The wafer 105 is then transferred to the scatterometer 440 for measurements. As described in greater detail below, the scatterometer 440 measures the wafer 105 to determine the acceptability and/or uniformity of the previously performed photolithography processes. The computer system 330, which is integrated with the APC framework, based on the wafer measurements, can adjust the recipe of the stepper 415, as needed. As will be recognized by those of ordinary skill in the art in light of this disclosure, the processing line 400 may include discrete or integrated processing tools for performing the processing steps described herein. The data acquired by the scatterometer 440 is used for making modifications to the control input signals on the line 323, which control the processing tools 320.

Figure 4B:
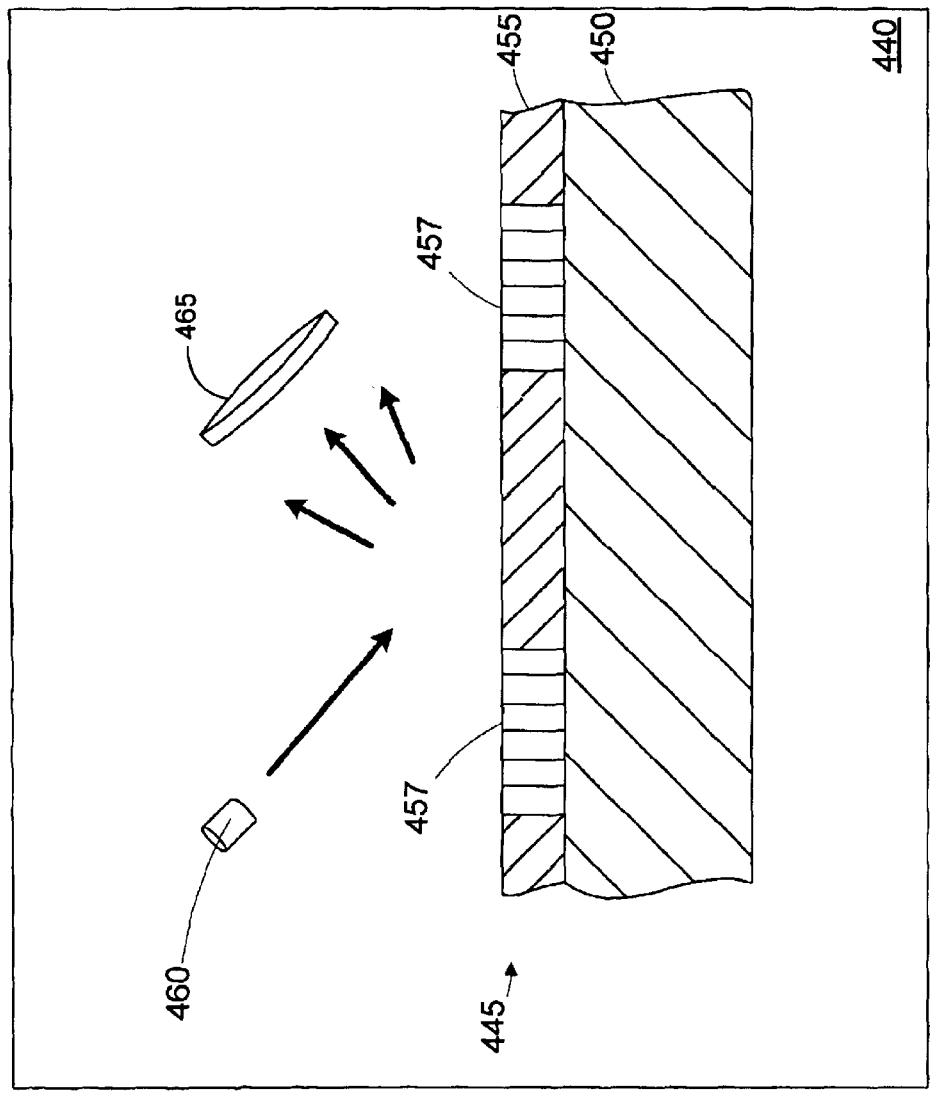
FIG. 4B illustrates a simplified view of a scatterometer with the semiconductor wafer loaded therein.

Referring to FIG. 4B, a simplified view of an illustrative scatterometer 440 with the wafer 105 loaded therein is provided. The wafer 105 has a base material 450. The photoresist layer 455 has regions 457 formed on the base material 450 resulting from the previous exposure and baking steps (i.e., referred to as a patterned photoresist layer 455). The chemical change resulting in the change in solubility of the regions 457 also results in the regions 457 having an index of refraction different than that of the unexposed portions of the photoresist layer 455.

In one embodiment, the scatterometer 440 comprises a light source 460 and a detector 465 positioned proximate the wafer 105. The light source 460 of the scatterometer 440 illuminates at least a portion of the wafer 105, and the detector 465 takes optical measurements, such as intensity, of the reflected light. Although the invention is described using a scatterometer 440 designed to measure reflected light intensity, it is contemplated that other measurement tools, such as an ellipsometer, a reflectometer, a spectrometer, or some other light-measuring device may be used. It is also contemplated that the scatterometer 440 may use monochromatic light, white light, or some other wavelength or combinations of wavelengths, depending on the specific implementation. The angle of incidence of the light may also vary, depending on the specific implementation.

The differences in the refractive indices for the regions 457 and the unexposed portions of the photoresist layer 455 cause light scattering, resulting in a decrease in the intensity of the reflected light as compared to scattering in the photoresist layer 455 before exposure and/or baking. The scatterometer 440 measures the intensity at different points on the wafer 105, such as on the periphery and in the middle.

A difference in the light intensity between various points indicates a nonconformity, such as a variation in the line widths of the regions 457. The light analyzed by the scatterometer 440 typically includes a reflected component and a scattered component. The reflected component corresponds to the light component where the incident angle equals the reflected angle. The scattered component corresponds to the light component where the incident angle does not equal the reflected angle. For purposes of discussion hereinafter, the term "reflected" light is meant to encompass both the reflected component and the scattered component.

Figure 1:
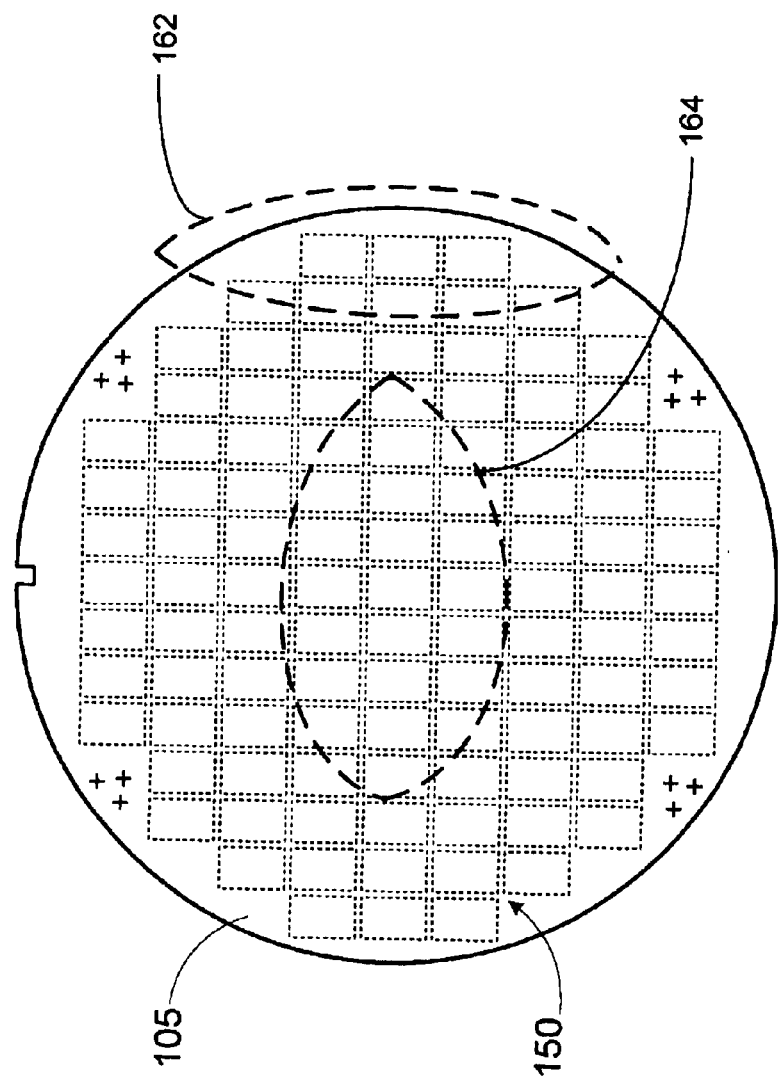
FIG. 1 is a simplified diagram of a prior art semiconductor wafer being processed.
Figure 2A:
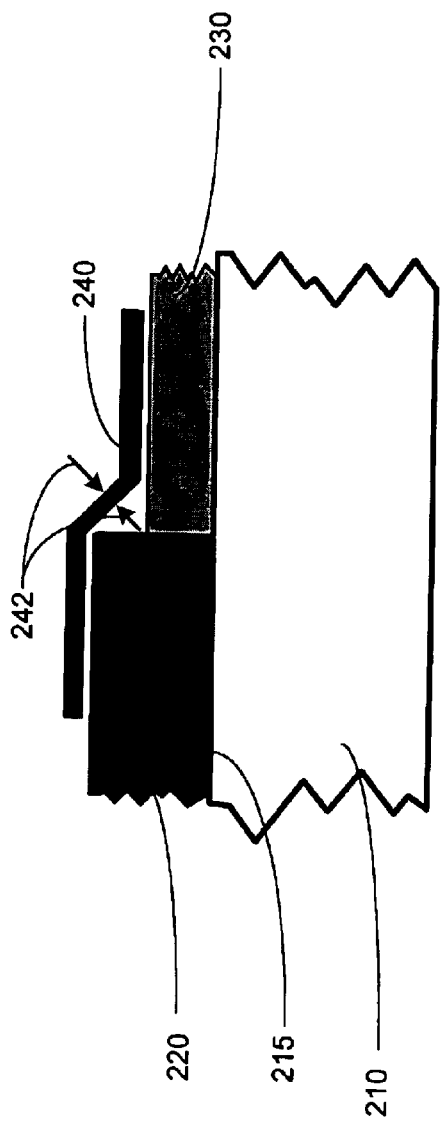
FIG. 2A is a cross-section view of a poly-silicon line structure placed on an area on a semiconductor wafer that transitions from a field region to an active region.
Figure 2B:
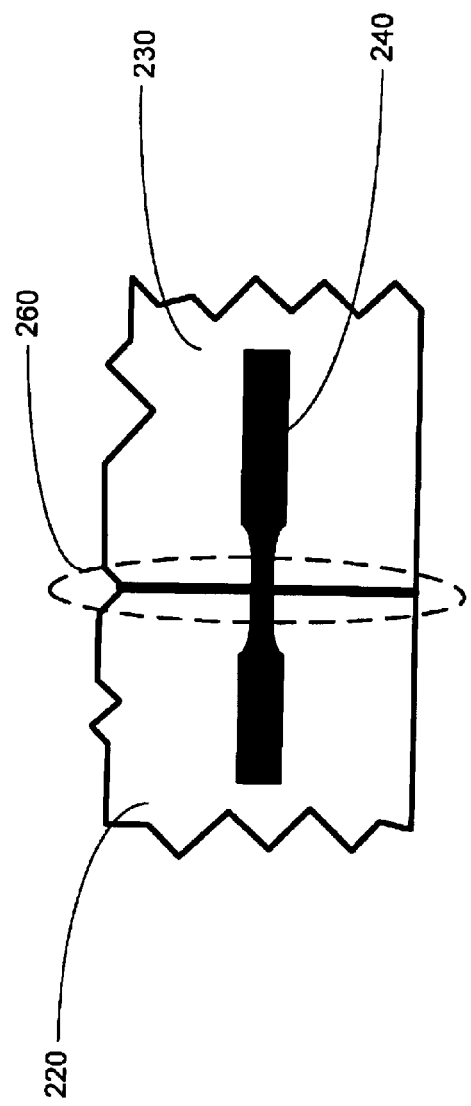
FIG. 2B is a top view of a poly-silicon line structure placed on an area on a semiconductor wafer that transitions from a field region to an active region.

The computer system 330, in conjunction with the manufacturing model 340, adjusts the recipe of the stepper 415 to correct the nonconformity. For example, if the intensity measurement on the periphery 162 of the wafer 105 (see FIG. 1) is greater than the intensity measurement in the middle 164, the line width is presumably less, because a smaller line width causes less scattering. To correct the line width variation, the computer system 330 changes the recipe of the stepper 415 such that the exposure sites (e.g., individual die or groups of die) with smaller line widths receive either an increased energy exposure or a longer duration exposure.

In an alternative embodiment, scatterometry measurements can be made before performing the develop process. Detecting variations and adjusting the stepper 415 recipe prior to the performing the develop process allows for a quicker corrective action response. It is contemplated that all wafers 105 in a lot may be tested, or only selected wafers 105 in the lot. Identifying variations early allows correction of wafers 105 within the same lot. For more stable steppers 415, the scatterometer 440 may be used only once per shift or once per week, depending on the specific implementation.

In the illustrated embodiment, the photoresist layer 455 is of a chemically-amplified type. In cases where a non-chemically-amplified photoresist material is used, the scatterometer 440 may be stationed prior to the oven 420. In a non-amplified photoresist system, the pattern is essentially complete after exposure in the stepper 415. The post exposure bake in the oven 420, which may be optional, is conducted to smooth the edges in the pattern resulting from standing waves, rather than to complete the patterning. Thus, the exposed portions already have an index of refraction different than the unexposed patterns, and the scatterometer 440 may be used. Scatterometry data is processed and correlated by the system 300 The scatterometry data is then analyzed by the scatterometry error analysis unit 170.

Figure 5:
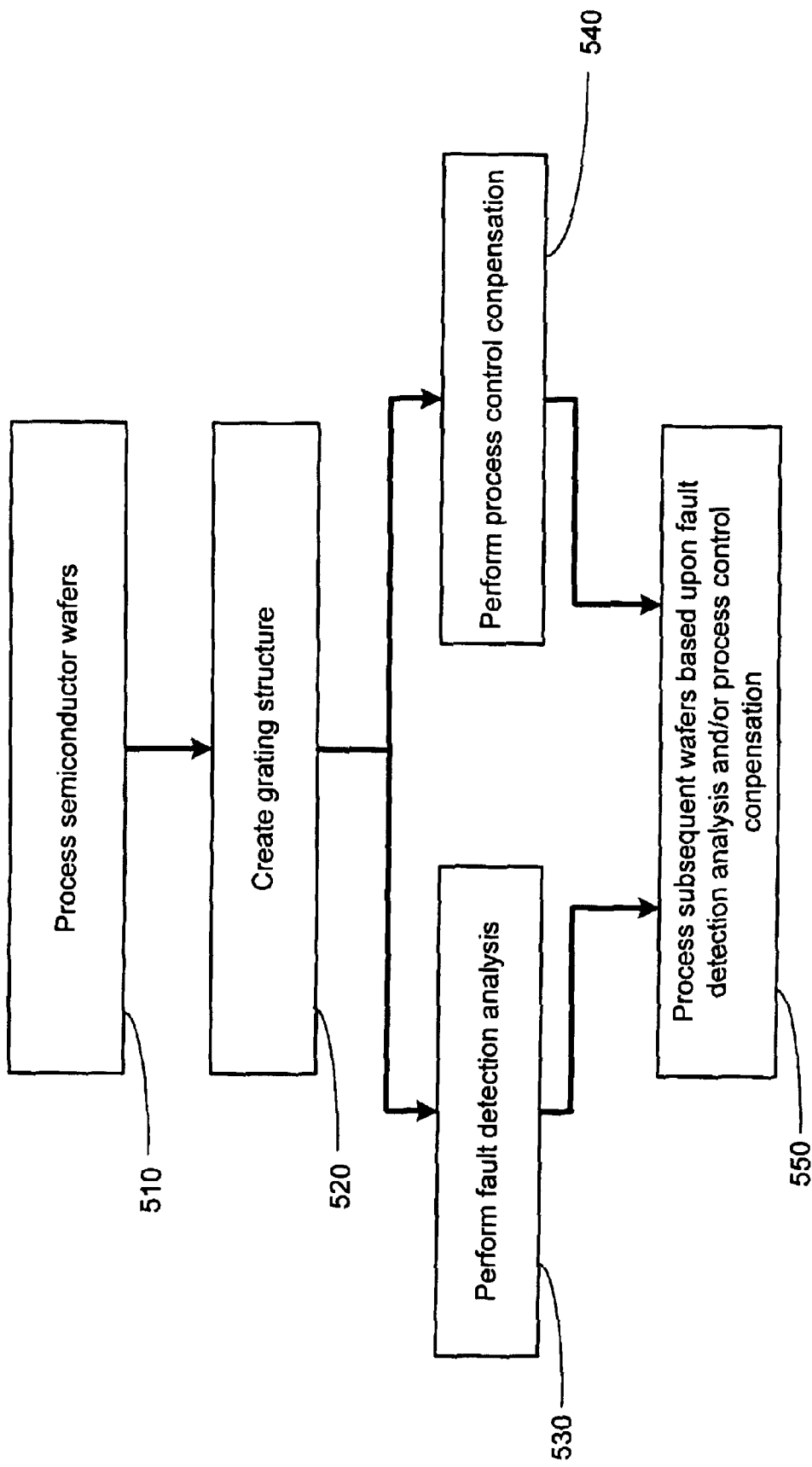
FIG. 5 illustrates a flowchart depiction of a method in accordance with one embodiment of the present invention.
Figure 6:
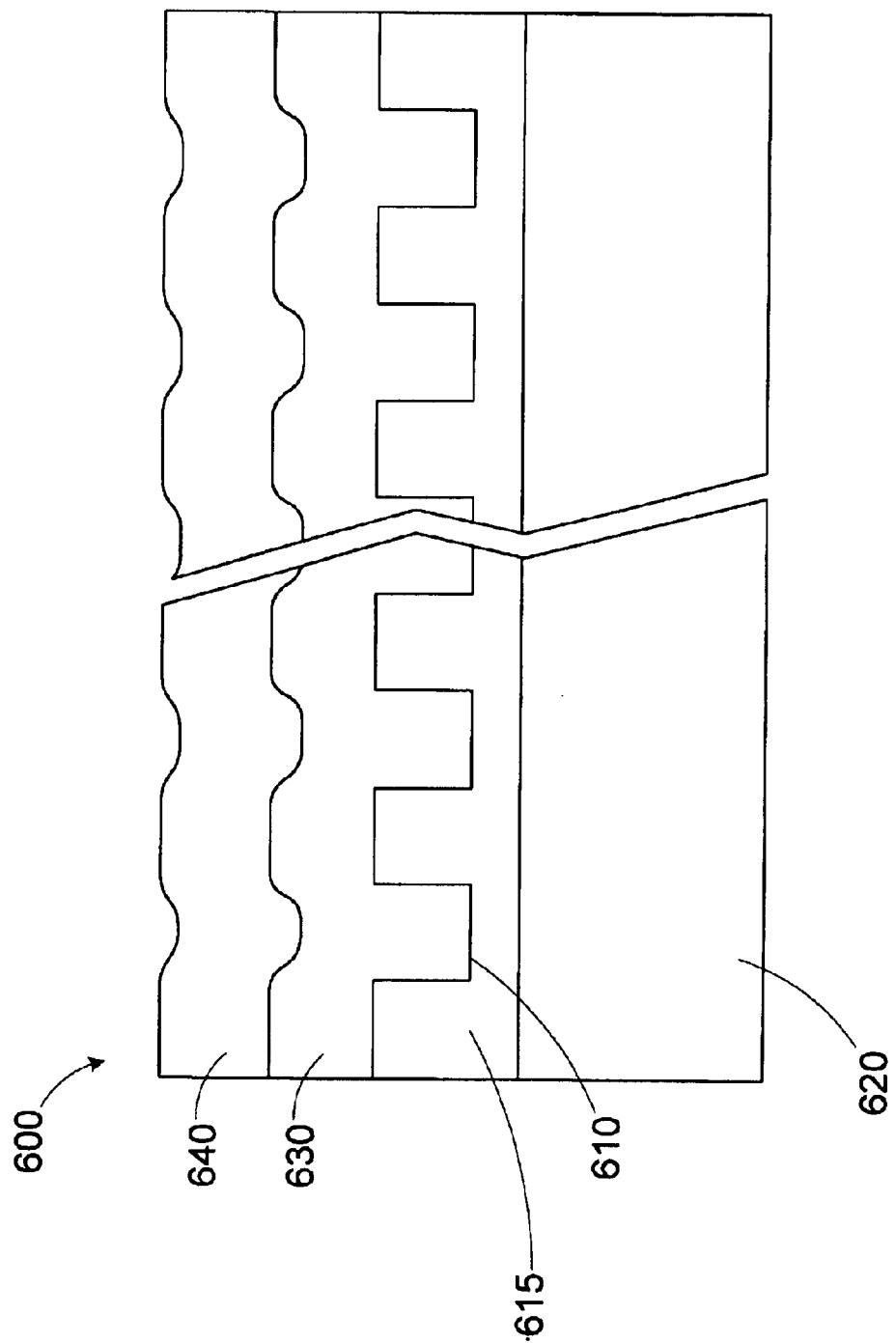
FIG. 6 is a cross section view of a grating structure after the formation of a silicon nitride stop layer and a silicon dioxide layer used to form grating features on the wafer of FIG. 1.

Turning now to FIG. 5, a flowchart depiction of one embodiment of the method in accordance with the present invention, is illustrated. Semiconductor wafers 105, or a manufacturing-lot of semiconductor wafers 150, are processed (block 510). In one embodiment, a photolithography process followed by an etching process is performed. During the processing of the semiconductor wafers 105, a grating structure is formed on the semiconductor wafer 105 being processed (block 520). In one embodiment, the grating structure is formed on the thickest photoresist layer on the semiconductor wafer 105. FIG. 6 illustrates a grating structure that is formed in a process layer 615 that is formed above a silicon substrate 620.

Figure 7A:
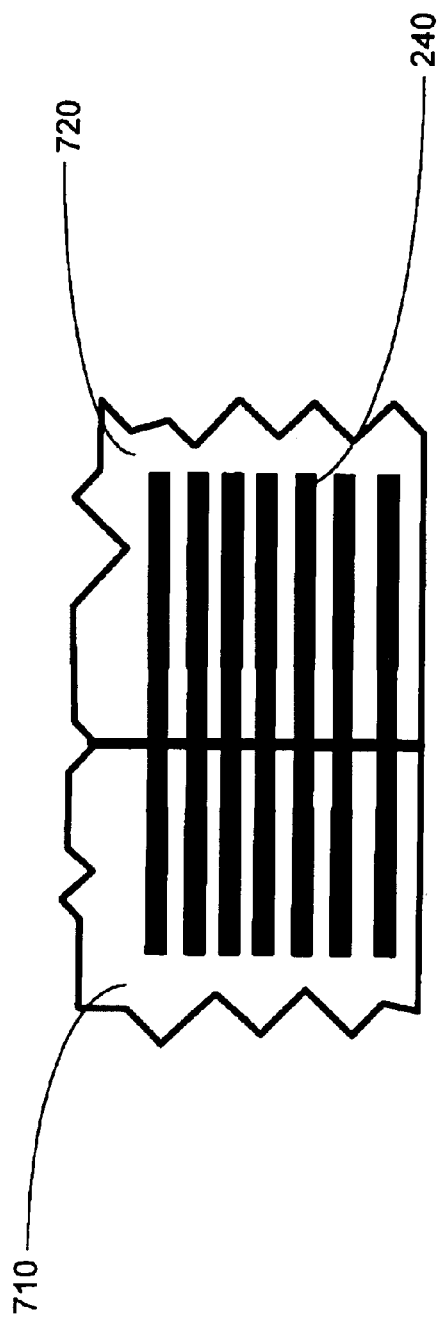
FIG. 7A illustrates a top view of a grating structure formed on the semiconductor wafer.

The grating structure illustrated in FIG. 6 is formed such that a portion of the grating structure 600 is located in a field region of the semiconductor wafer 105 being processed, and a portion of the grating structure 600 is located in an active region of the semiconductor wafer 105. In one embodiment, the grating structure 600 can be within scribe lines. In an alternative embodiment, the grating structure 600 a part of a process section. Turning now to FIG. 7, the grating structure 600 that overlaps a field region and an active region is shown. FIG. 7A shows a field region 710 and an active region 720 that are formed on the semiconductor wafer 105 being processed. In one embodiment the field region 710 may be made from field oxide material, such as silicon oxide. Generally, a field region 710 electrically isolates one active region 720 from another active region. The active regions 720 generally comprise transistors and other electrically active areas, such as the collector of a transistor. Poly-silicone lines 240 are used to electrically connect one active region 720 with another.

Figure 7B:
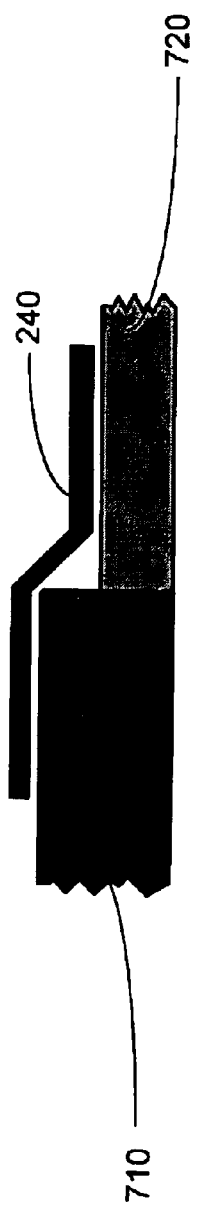
FIG. 7B illustrates a cross-sectional view of the grating structure formed on the semiconductor wafer.

Generally, there is a step down from the height of the field region 710 to a lower height of the active region 720. FIG. 7B illustrates the step down from the field region 710 to the active region 720. The poly-silicon lines 240 that are formed across the field region 710 and the active region 720 experience a step down at the intersection of the active region 720 and the field region 710, as shown in FIG. 7B. Therefore, the poly-silicon lines 240 can experience a necking effect at the step down region at the intersection of the field region 710 and the active region 720. The grating structure 600 formed on the silicon wafer experiences a step down from the field region 710 to the active region 720. This grating structure 600 can be used to detect necking or breaking problems that may occur on the poly-silicon line 240 on the semiconductor wafer 105 being processed.

Once the grating structure 600 that overlaps the field region 710 and the active region 720 is in place, further error analysis can be performed. In one embodiment, a fault detection process is performed by the system 300 (block 530). A flowchart depiction of the steps for performing the fault detection process indicated in block 530 of FIG. 5, is shown in FIG. 8.

Turning now to FIG. 8, a time interval in which to perform a fault detection analysis on semiconductor wafers 105 being processed, is determined by the system 300 (block 810). Generally, fault detection analyses are perform ed to detect significant, or gross, errors that occur during semiconductor processing. In order to reduce the possibility of gross errors occurring during manufacturing, semiconductor wafers 105 that are being processed are generally examined at a predetermined time interval. Those who are skilled in the art and have the benefit of the present disclosure can determine such a time interval. When a time interval for performing fault detection analysis is determined, at least on e semiconductor wafer 105 is selected for scatterometry analysis (block 820). A more detailed description of the steps of performing the scatterometry analysis described in block 820 is provided below.

After performing a scatterometry analysis process, the system 300 determines whether a significant deviation from predetermined specifications has occurred in the semiconductor device that was examined (block 830). Those skilled in the art and have benefit of the present disclosure can define the predetermined specifications. In one embodiment, a data comparison of the acquired metrology data and the data from the scatterometry reference library 365 is performed in order to determine whether there exists a significant deviation. When a determination is made that a significant deviation has occurred, the error is reported to the computer system 130. Operators of the system 300 can then be notified of the error report and make appropriate corrective measures, such as modifying control input parameters for subsequent processes (block 840). When a determination is made that there has been no significant deviation in the performance of the process, the system 300 waits during a time period prescribed by the predetermined time interval before performing a subsequent fault detection check (block 850).

Figure 9:
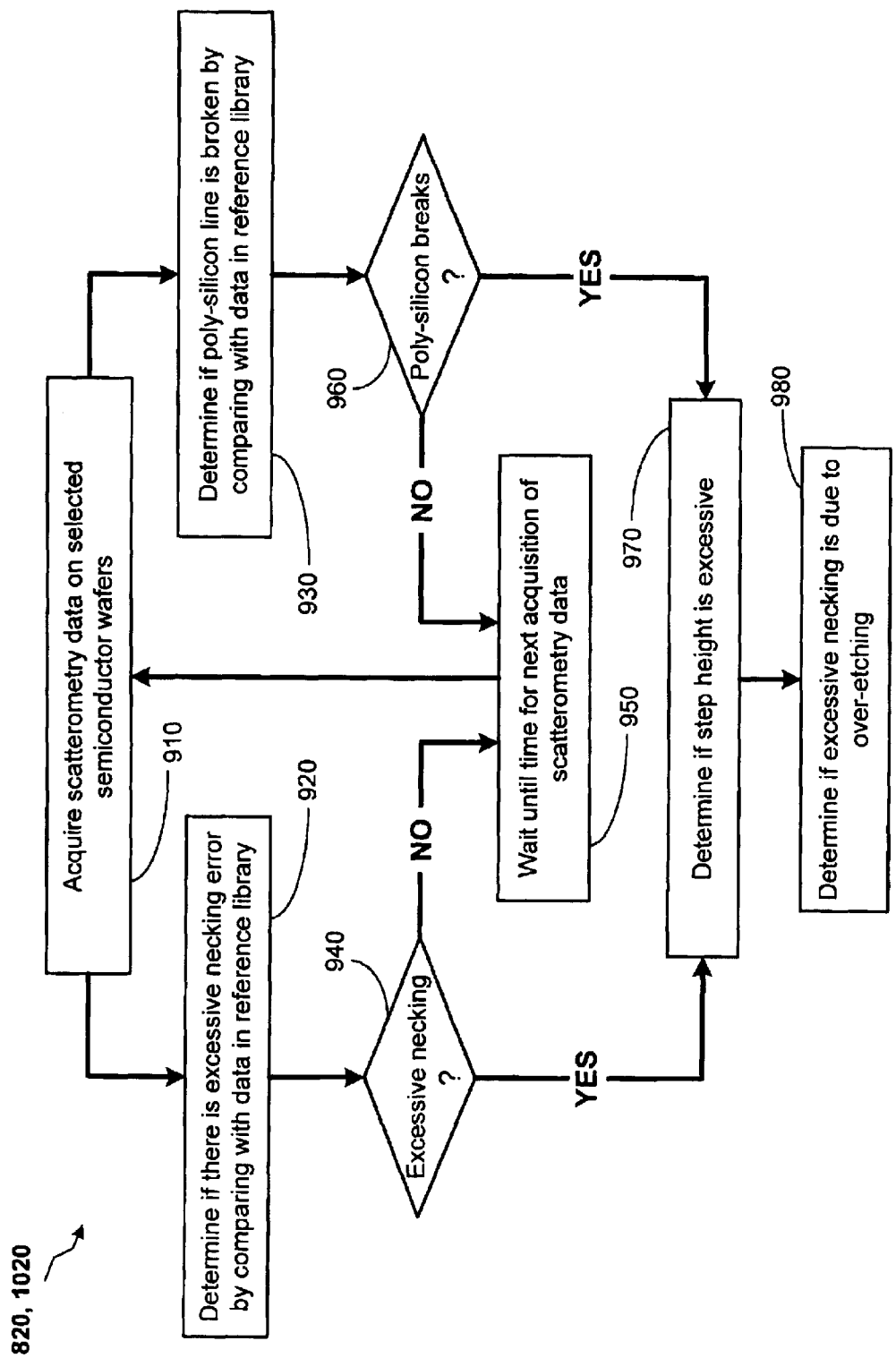
FIG. 9 illustrates a flowchart depiction of a method of performing a scatterometry analysis described in FIG. 8, in accordance with one embodiment of the present invention.

Turning now to FIG. 9, a flowchart depiction of the steps of performing the scatterometry analysis described in block 820 of FIG. 8, is illustrated. In one embodiment, using the scatterometry techniques described above, scatterometry data relating to the selected semiconductor wafers 105, is acquired (block 910). Using optical data acquisition techniques, such as angle reflectometry or spectroscopic ellipsometry, an optical signature that relates to characteristics of the structure on the semiconductor wafer 105 being examined can be determined. The scatterometry data acquired from the semiconductor wafer 105 being examined is compared to the scatterometry data (e.g., optical signatures) stored in the scatterometry reference library 365. In one embodiment, the computer system 130 performs such a comparison.

Using the comparison of the scatterometry reference data stored in the scatterometry reference library 365, and the scatterometry data acquired from the semiconductor wafer 105 being analyzed, the system 300 makes a determination whether there is significant or excessive necking on the poly-silicon lines 240 associated with the grating structure 600 that is developed across the field region 710 and the active region 720 (block 920). Furthermore, the system 300 uses the scatterometry data acquired from the semiconductor wafer 105 being analyzed and the scatterometry reference data in the scatterometry reference library 365 to determine whether a break in the poly-silicon line 240 associated with the grating structure 600 has occurred (block 930).

When a determination is made that there that are no significant necking errors as a result of the scatterometry data comparison, the system 300 waits to perform the next scatterometry analysis as indicated by the flowchart-path: from block 940; to block 950; and onto block 910. Similarly, when a determination is made that there are no broken poly-silicon lines 240 associated with the grating structure 600, the system 300 waits until the next scatterometry analysis as indicated from the flowchart-path: from block 960; to block 950; and onto block 910.

When the system 300 makes a determination, that there is a significant necking error, or there is a broken poly-silicon line 240 error, associated with the grating structure 600, the system 300 determines whether the step height between the field region 710 and the active region 720 is excessively high (block 970). This determination can be made by those skilled in the art who had the benefit of the present disclosure. Furthermore, the system 300 makes a determination whether the necking error or the broken poly-silicon line 240 error associated with the grating structure 600, may have been caused due to over-etching (block 980).

Turning back to FIG. 5, in addition to the fault detection analysis described in block 430 of FIG. 5, the system 300 also performs a process control compensation procedure, as indicated in block 540 of FIG. 5. A flowchart depiction of one embodiment of the steps for performing the process control compensation described in block 540, is illustrated in FIG. 10.

Figure 10:
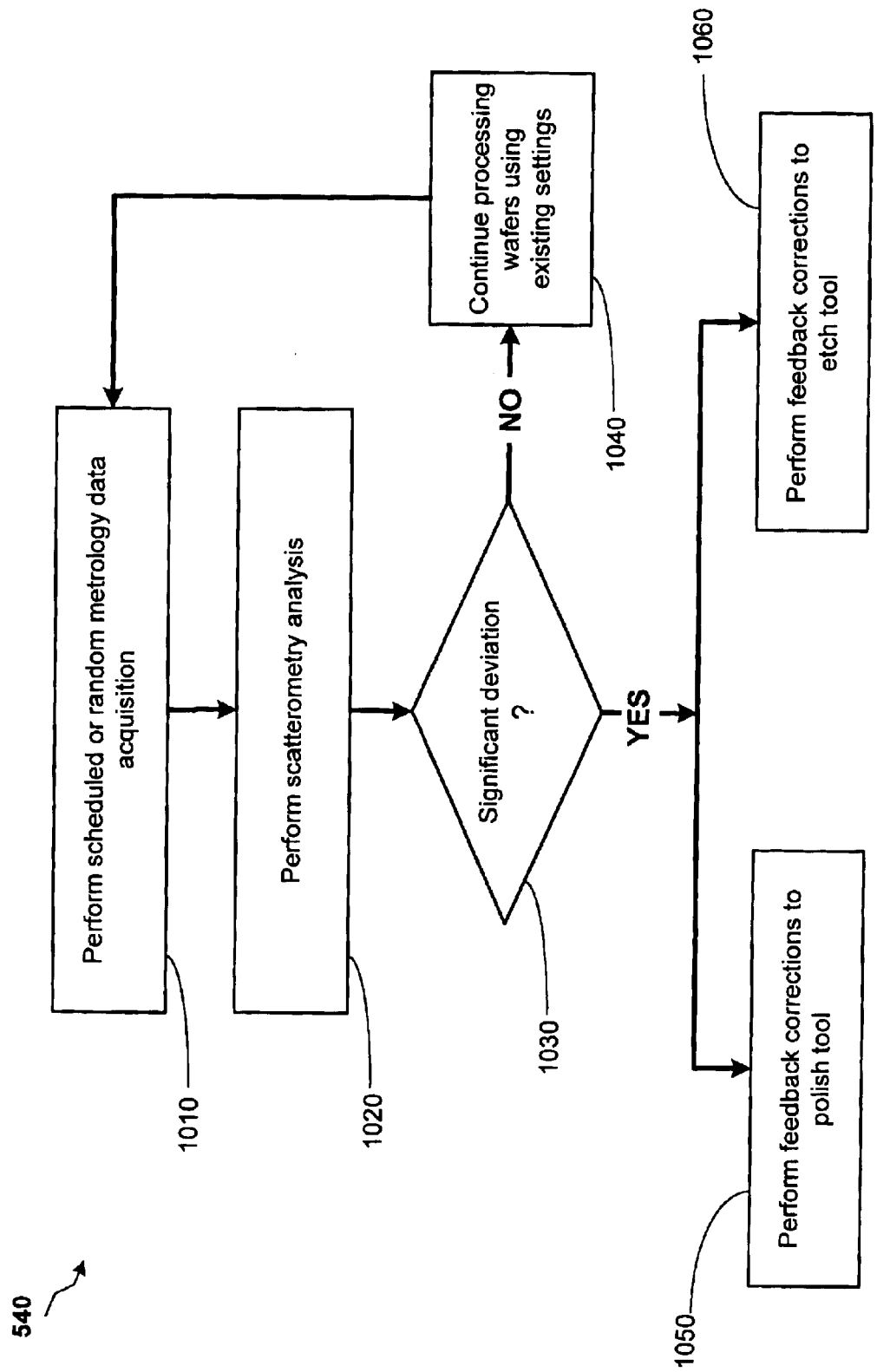
FIG. 10 illustrates a flowchart depiction of a method of performing a process control compensation process described in FIG. 5, in accordance with one embodiment of the present invention While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

Turning now to FIG. 10, the system 300 performs a scheduled, or in an alternative embodiment, a random metrology data acquisition process, on semiconductor wafers 105 being processed (block 1010). In one embodiment, the metrology data is acquired by the metrology tool 350. In one embodiment a scatterometry metrology device is used to acquire the metrology data. When the metrology data is acquired, a scatterometry analysis is performed using the acquired metrology data (block 1020). The scatterometry analysis indicated in block 1020 of FIG. 10 is substantially similar to the scatterometry analysis indicated in FIG. 9, which is described above.

Once the scatterometry analysis performed, the system 300 makes a determination whether a significant deviation resulting from a scatterometry analysis has taken place (block 1030). When a determination is made that there is no significant deviation in comparison with predetermined specification, the system 300 continues the processing of semiconductor wafers 105 using the existing settings (block 1040). When the system 300 determines that there is a significant deviation resulting from the scatterometry analysis, in one embodiment, the system 300 performs feedback corrections to a processing tool 320 that performs a polishing function (block 1050). The feedback corrections to the polishing tool can be used to reduce the step height between the field region 710 and the active region 720. In one embodiment, feedback modifications can be sent a polishing tool to increase the polishing of the field region 710 in order to reduce the height of the field region 710, thereby decreasing the step height between the field region 710 and the active region 720.

In an alternative embodiment, feedback corrections can be made to a processing tool 320 that performs an etch function (block 1060). In one embodiment, in order to reduce the necking errors or breaking errors in the poly-silicon line 240, feedback control modifications to an etch tool can be used to prompt the etch tool to reduce the amount of etching of poly-silicon lines 240 on the semiconductor wafer 105. Therefore, thicker poly-silicon lines 240 would result and would be less likely to experience necking errors or breaking errors. The feedback corrections described above can be performed using the system 300 described in FIG. 3. Turning back to FIG. 5, once the fault detection process, or alternatively, the process control compensation process, are substantially complete, subsequent processing of semiconductor wafers 105 are performed based upon the results from the fault detection process and the process control compensation process (block 450).

The principles taught by the present invention can be implemented in an Advanced Process Control (APC) Framework. The APC is a preferred platform from which to implement the control strategy taught by the present invention. In some embodiments, the APC can be a factory-wide software system, therefore, the control strategies taught by the present invention can be applied to virtually any of the semiconductor manufacturing tools on the factory floor. The APC framework also allows for remote access and monitoring of the process performance. Furthermore, by utilizing the APC framework, data storage can be more convenient, more flexible, and less expensive than local drives. The APC platform allows for more sophisticated types of control because it provides a significant amount of flexibility in writing the necessary software code.

Deployment of the control strategy taught by the present invention onto the APC framework could require a number of software components. In addition to components within the APC framework, a computer script is written for each of the semiconductor manufacturing tools involved in the control system. When a semiconductor manufacturing tool in the control system is started in the semiconductor manufacturing fab, it generally calls upon a script to initiate the action that is required by the process controller, such as the overlay controller. The control methods are generally defined and performed in these scripts. The development of these scripts can comprise a significant portion of the development of a control system. The principles taught by the present invention can be implemented into other types of manufacturing frameworks.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A system, comprising:
 a computer system;
 a manufacturing model coupled with said computer system, said manufacturing model being capable of generating and modifying at least one control input parameter signal;
 a machine interface coupled with said manufacturing model, said machine interface being capable of receiving process recipes from said manufacturing model;
 a processing tool capable of processing semiconductor wafers and being operatively coupled to said machine interface, said processing tool being capable of receiving at least one control input parameter signal from said machine interface;
 a metrology tool coupled with said processing tool, said metrology tool being capable of acquiring metrology data;
 a scatterometry reference library, said scatterometry reference library comprising optical data related to a plurality of poly-silicon structures; and
 a scatterometry data error analysis unit coupled to said metrology tool and said scatterometry reference library, said scatterometry data error analysis unit capable of comparing said metrology data from the metrology tool, to corresponding data in said scatterometry reference library, and calculating at least one of a necking error and a poly-silicon structure break error in response to said comparison.

2. A system, comprising:
 a processing tool for processing at least one semiconductor wafer;
 a metrology tool to acquire data relating to processing of said semiconductor wafer;
 a controller operatively coupled to said processing tool and said metrology tool, said controller to:
  access data from a reference library comprising optical data relating to a poly-silicon formation on a semiconductor wafer;
  compare said metrology data to data from said reference library; and
  perform a fault-detection analysis in response to said comparison of said metrology data and said reference library data for improving processing of a subsequent semiconductor wafer.

3. The system of claim 2, further comprising:
 a computer system;
 a manufacturing model coupled with said computer system, said manufacturing model being capable of generating and modifying at least one control input parameter signal;
 a machine interface coupled with said manufacturing model, said machine interface being capable of receiving process recipes from said manufacturing model;
 said processing tool being operatively coupled to said machine interface, said processing tool being capable of receiving at least one control input parameter signal from said machine interface;
 said metrology tool coupled with said processing tool, said metrology tool being capable of acquiring metrology data;
 a scatterometry reference library, said scatterometry reference library comprising optical data related to a plurality of poly-silicon structures; and
 a scatterometry data error analysis unit coupled to said metrology tool and said scatterometry reference library, said scatterometry data error analysis unit capable of comparing said metrology data from the metrology tool, to corresponding data in said scatterometry reference library, and calculating at least one of a necking error and a poly-silicon structure break error in response to said comparison.

4. The system of claim 3, wherein said computer system is capable of generating modification data for modifying at least one control input parameter in response to said calculation of at least one of a necking error and a poly-silicon structure break error.

5. The system of claim 4, wherein said manufacturing model is capable of modifying said control input parameter in response to said modification data.

6. The system of claim 3, wherein said metrology tool is a scatterometer.

7. An apparatus, comprising:
 a controller to control an operation of a processing tool and a metrology tool, said controller to:
  acquire metrology data relating to processing of a semiconductor wafer in said processing tool, from said metrology tool;
  access data from a reference library comprising optical data relating to a poly-silicon formation on a semiconductor wafer;
  compare said metrology data to data from said reference library; and
  perform a fault-detection analysis in response to said comparison of said metrology data and said reference library data for improving processing of a subsequent semiconductor wafer.

8. The apparatus of claim 7, wherein said controller comprises a computer system that is capable of generating modification data for modifying at least one control input parameter in response to a calculation of at least one of a necking error and a poly-silicon structure break error from said fault detection analysis.

9. The apparatus of claim 8, further comprising a manufacturing model that is capable of modifying said control input parameter in response to said modification data.

* * * * *

UNITED STATES PATENT AND TRADEMARK OFFICE
CERTIFICATE OF CORRECTION

PATENT NO.    : 6,766,215 B1
DATED         : July 20, 2004
INVENTOR(S)   : Kevin R. Lensing and Marilyn I. Wright It is certified that error appears in the above-identified patent and that said Letters Patent is hereby corrected as shown below:

Column 2,
Line 21, insert a period after "2B".

Column 3,
Line 65, insert a period after "invention".

Column 4,
Line 48, replace "31a" with -- 315a --.

Column 7,
Line 47, insert a period after "300".

Column 8,
Lines 47-48, replace "on e" with -- one --.

Signed and Sealed this

Fourteenth Day of December, 2004

JON W. DUDAS
*Director of the United States Patent and Trademark Office*